(12) United States Patent
Dwyer et al.

(10) Patent No.: US 11,685,912 B2
(45) Date of Patent: Jun. 27, 2023

(54) AFFINITY PURIFICATION OF GLYCOSIDASE-CLEAVING ENZYMES

(71) Applicant: TAKEDA PHARMACEUTICAL COMPANY LIMITED, Osaka (JP)

(72) Inventors: Brian Dwyer, Lexington, MA (US); Bohong Zhang, Lexington, MA (US); Jun Hu, Lexington, MA (US); Muthuraman Meiyappan, Lexington, MA (US); Thomas Miller, Lexington, MA (US); Paul McLean, Lexington, MA (US); Clark Pan, Lexington, MA (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/978,417

(22) PCT Filed: Mar. 5, 2019

(86) PCT No.: PCT/US2019/020690
§ 371 (c)(1),
(2) Date: Sep. 4, 2020

(87) PCT Pub. No.: WO2019/173293
PCT Pub. Date: Sep. 12, 2019

(65) Prior Publication Data
US 2021/0040465 A1    Feb. 11, 2021

Related U.S. Application Data

(60) Provisional application No. 62/639,062, filed on Mar. 6, 2018, provisional application No. 62/695,543, filed on Jul. 9, 2018.

(51) Int. Cl.
*C12N 9/40*    (2006.01)
*B01J 20/286*    (2006.01)
(Continued)

(52) U.S. Cl.
CPC .......... *C12N 9/2465* (2013.01); *B01J 20/286* (2013.01); *B01J 20/289* (2013.01);
(Continued)

(58) Field of Classification Search
CPC .... B01J 20/286; B01J 20/289; B01J 20/3253; B01J 20/3255; B01J 20/3219; C12Y 302/01022; C12N 9/2465; C07K 1/22
See application file for complete search history.

(56) References Cited

FOREIGN PATENT DOCUMENTS

WO        199008584        8/1990

OTHER PUBLICATIONS

International Search Report dated Aug. 5, 2019 in connection with PCT/US19/20690.
(Continued)

*Primary Examiner* — Vishal V Vasisth
(74) *Attorney, Agent, or Firm* — Troutman Pepper Hamilton Sanders LLP

(57) ABSTRACT

The invention relates to an affinity resin functionalized with small molecule inhibitors of glycoside-cleaving enzymes, e.g., α-galactosidase A (α-Gal A), glucocerebrosidase (GCB), β-galactosidase, and acid alpha-glucosidase (GAA), and a method for purifying glycoside-cleaving enzymes produced in a cell line using the small molecule inhibitor-functionalized affinity resin.

34 Claims, 7 Drawing Sheets

(51) Int. Cl.
    *B01J 20/289* (2006.01)
    *B01J 20/32* (2006.01)
(52) U.S. Cl.
    CPC ....... *B01J 20/3219* (2013.01); *B01J 20/3253* (2013.01); *B01J 20/3255* (2013.01); *C12Y 302/01022* (2013.01)

(56) References Cited

OTHER PUBLICATIONS

Written Opinion dated Aug. 5, 2019 in connection with PCT/US19/20690.

Baindur et al., "Solution-Phase Synthesis of a Library of 3, 5, 7-Trisubstituted 3H-[1,2,3]triazolo[4,5-d]pyrimidines," Journal of Combinatorial Chemistry, Jul. 18, 2003, vol. 5, pp. 653-659, Abstract.

Pubmed Substance Record for SID 329758054, "StratoSpheres(TM PL-PIP (Piperidine) resin, 50-100 mesh, extent of labeling: 3.0-4.0 mmol/g loading, 1% cross-linked," U.S. National Library of Medicine, Mar. 3, 2017 (https://pubchem.ncbi.nlm.nih.gov/substance/329758054); p. 1.

Trapero et al. "Adamantane substituted aminocyclitols as pharmacological chaperones for Gaucher disease," MedChemComm, Oct. 1, 2013, vol. 4, pp. 1584-1589; p. 1585.

Harrak et al. "Aminocyclytol-Substituted Phytoceramides and their Effects on iNKT Cell Stimulation," MedChemComm, Sep. 28, 2009, vol. 4, pp. 1608-1613; p. 1608.

Bause et al. "N-Methyl-N-(5-carboxypentyl)-1-deoxynojirimycin, a new affinity ligand for the purification of trimming glucosidase I," FEBS Letters, Jan. 28, 1991, vol. 278, pp. 167-170; p. 167, p. 169.

Fazldeen H., et al., "ChemInform Abstract: A New Sepharose Derivative Containing Covalently Bound Myo-Inositol: Its Structure and Application" Chemischer Informationsdienst, vol. 10, No. 51, Jan. 10, 1979, pp. 823-830.

Extended European Search Report dated Nov. 10, 2021 in connection with EP Application No. 19765012.0.

Fazldeen H., et al., "ChemInform Abstract: A New Sepharose Derivative Containing Covalently Bound Myo-Inositol: Its Structure and Application" Chemischer Informationsdienst, vol. 10, No. 51, Jan. 10, 1979, pp. 823-830.

Koller F. et al., "Myo-Inositol Oxygenase from Rat Kidneys, I: Purification by Affinity Chromatography; Physical and Catalytic Properties", Hoppe-Seyler's Zeitschrift Fuer Physiologische Chemie, vol. 360, No. 1, Apr. 1, 1979, pp. 507-513.

Koller F. et al., "Herstellung Einer Spezifish Sustituierten Sepharose Zur Affinitaetschromatographic Von Enzymen, Die Myco-Inosit Umsetzen/Synthesis of a Specifically Substituted Sepharose Derivative for the Affinity Chromatography of Enzymes Acting on Myo Inositol", Monatshefte Fur Chemie/Chemical Monthly, Springer Vienna, Vienna, vol. 105, No. 2, Jan. 1, 1974, pp. 379-381.

Moise A. et al., "Substrate and Substrate-Mimetic Chaperone Binding Sites in Human [alpha]-Galactosidase A Revealed by Affinity-Mass Spectrometry", Journal of the American Society for Mass Spectrometry, Elsevier Science Inc, US, vol. 27, No. 6, Apr. 25, 2016, pp. 1071-1078.

Pearson W.H. et al., "Preparation of immobilized swainsonine analogs on solid support", Tetrahedron Letters, Elsevier, Amsterdam, NL, vol. 43, No. 12, Mar. 18, 2002, pp. 2175-2178.

AFFINITY PURIFICATION OF GLYCOSIDASE-CLEAVING ENZYMES

CROSS-REFERENCE TO RELATED APPLICATIONS

This application is a 371 National Stage of PCT/US19/20690, filed Mar. 5, 2019, which claims priority pursuant to 35 U.S.C. § 119(e) to U.S. Provisional Application No. 62/639,062, filed Mar. 6, 2018, and U.S. Provisional Application No. 62/695,543, filed Jul. 9, 2018, the disclosures of which are herein incorporated by reference in their entirety.

FIELD OF INVENTION

The present invention relates to affinity resins functionalized with small molecule inhibitors of glycoside-cleaving enzymes, e.g., α-galactosidase A (α-Gal A), glucocerebrosidase (GCB), β-galactosidase, and acid alpha-glucosidase (GAA), and methods for purifying glycoside-cleaving enzymes produced in a cell line using the small molecule inhibitor-functionalized affinity resins.

BACKGROUND OF THE INVENTION

Fabry disease is caused by a deficiency in the enzyme α-galactosidase A (α-Gal A): The pathophysiology of Fabry Disease is well established: due to a lack of the lysosomal enzyme α-galactosidase A (α-Gal A), there is accumulation of globotriaosylceramide (Gb3) throughout the body.

Enzyme replacement therapy ("ERT") is a currently used method of treatment for Fabry disease. Two α-Gal A products are commercially available for the treatment of Fabry disease: agalsidase alfa (Replagal®, Shire Human Genetic Therapies) and agalsidase beta (Fabrazyme®; Genzyme Corporation). These two forms of ERT effectively compensate for a patient's inadequate α-Gal A activity with a recombinant form of the enzyme, administered intravenously.

The cDNA and gene encoding human α-Gal A have been isolated and sequenced. Human α-Gal A is expressed as a 429-amino acid polypeptide, of which the N-terminal 31 amino acids are the signal peptide. The human enzyme has been expressed in Chinese Hamster Ovary (CHO) cells (Desnick et al., U.S. Pat. No. 5,356,804; Ioannou et al., J Cell Biol. 119: 1137 (1992)); insect cells (Calhoun et al., WO 90/11353); and human cells (Selden et al., U.S. Pat. Nos. 6,083,725 and 6,458,574).

Recombinant α-Gal A is produced in a mammalian cell line by genetic engineering technology. The mature enzyme that is secreted in the cell culture media is a homodimeric glycoprotein, with each subunit consisting of 398 amino acids after removal of a 31-residue signal sequence. The protein undergoes post-translational modification by and the addition of 3 N-linked carbohydrate chains.

1-deoxygalactonojirimycin ("DGJ") and its salt, 1-deoxygalactonojirimycin hydrochloride (also known by its United States Adopted Name (USAN), migalastat hydrochloride) acts as a pharmacological chaperone for mutant α-Gal A by selectively binding to the enzyme, thereby increasing its stability and helping the enzyme fold into its correct three-dimensional shape. This stabilization of α-Gal A allows the cell's quality control mechanisms to recognize the enzyme as properly folded so that trafficking of the enzyme to the lysosome is increased, allowing it to carry out its intended biological function, the metabolism of Globotriaosylceramide (GL-3). The chemical structure of DGJ is shown below:

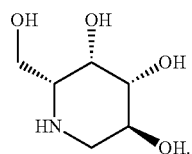 [SMILES: OC[C@H]1NC[C@H](O)[C@@H](O)[C@H]1O]

Purification of α-Gal A by affinity column chromatography using Concanavalin A (Con A)-Sepharose and immobilized thio-α-galactoside (thio-Gal) has been disclosed (see Yasuda et al. Prot. Expr. & Purif. 2004, 37, 499-506). However, this and other reported methodology for purification of α-Gal A has a number of serious drawbacks, such as requiring multi-step manipulation of raw material, requiring costly elution solutions, and/or not being easily scalable.

Gaucher disease is an autosomal recessive lysosomal storage disorder characterized by a deficiency in the lysosomal enzyme, glucocerebrosidase (GCB). GCB hydrolyzes the glycolipid glucocerebroside that is formed after degradation of glycosphingolipids in the membranes of white blood cells and red blood cells. The deficiency in this enzyme causes glucocerebroside to accumulate in large quantities in the lysosomes of phagocytic cells located in the liver, spleen and bone marrow of Gaucher patients. Accumulation of these molecules causes a range of clinical manifestations including splenomegaly, hepatomegaly, skeletal disorder, thrombocytopenia and anemia. (Beutler et al. Gaucher disease; In: The Metabolic and Molecular Bases of Inherited Disease (McGraw-Hill, Inc., New York, 1995) pp. 2625-2639)

Treatments for patients suffering from this disease include administration of analgesics for relief of bone pain, blood and platelet transfusions and, in some cases, splenectomy. Joint replacement is sometimes necessary for patients who experience bone erosion.

Enzyme replacement therapy with GCB has been used as a treatment for Gaucher disease. Current treatment of patients with Gaucher disease includes administration of Velaglucerase, available under the name VPRIV® from Shire Human Genetic Therapies.

Velaglucerase is human beta-glucocerebrosidase produced by gene-activation in a human cell line. Gene activation refers to targeted recombination with a promoter that activates the endogenous beta-glucocerebrosidase gene in the selected human cell line. Velaglucerase is secreted as a monomeric glycoprotein of approximately 63 kDa and is composed of 497 amino acids with a sequence identical to the natural human protein. The amino acid sequence of velaglucerase is described in Zimran et al. (2007) Blood Cells Mol Dis, 39: 115-118. As with α-Gal A, purification of GCB has a number of serious drawbacks, such as requiring multi-step manipulation of raw material, requiring costly elution solutions, and/or not being easily scalable.

Conduritol B epoxide is an inhibitor of GCB. The chemical structure of Conduritol B is shown below:

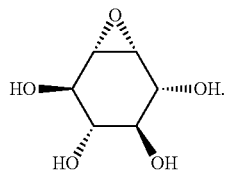

The epoxide of Conduritol B reacts covalently with the enzyme active site. A series of competitive (reversible) inhibitors referred to as amino myo-inositols have been described, which have close similarity to Conduritol, except that they do not react chemically with the enzyme (see Trapero et al. J. Med. Chem. 2012, 55, 4479-4488).

Glycogen storage disease type II, also called Pompe disease, is an autosomal recessive metabolic disorder which damages muscle and nerve cells throughout the body. It is caused by an accumulation of glycogen in the lysosome due to deficiency of the lysosomal acid alpha-glucosidase enzyme (GAA). Pompe disease can be treated by enzyme replacement therapy using biologically active recombinant human acid alpha-glucosidase commercially available as Myozyme® or Lumizyme® (Genzyme Corporation).

Thus, there exists an unmet need for novel methods for purifying glycoside-cleaving enzymes, such as α-Gal A, GCB, and GAA, that are easily scalable, require no manipulation of raw material, and minimize production costs.

SUMMARY OF THE INVENTION

Various non-limiting aspects and embodiments of the invention are described below.

In one aspect of the present invention, an affinity resin is provided, comprising a small molecule ligand having the formula:

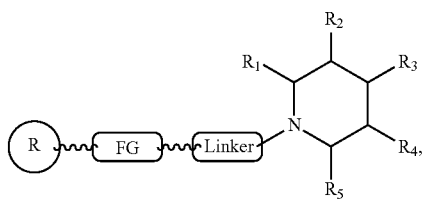

wherein R is a resin matrix;
FG is absent or is a functional group selected from —O—, —NH—, —C(O)N—, —C(O)O—, CH$_2$, and —S—;
Linker is absent or is selected from a straight chained, branched or cyclic aliphatic $C_2$-$C_{20}$ hydrocarbon; a heteroaliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S and combinations thereof;
$R_1$, $R_2$, $R_3$, $R_4$, and $R_5$ are each independently selected from H, OH, CH$_2$OH and —NH—C(O)—CH$_3$, and
wherein the affinity resin is capable of binding a glycoside-cleaving enzyme.

In some embodiments, the affinity resin is capable of binding a glycoside-cleaving enzyme from conditioned medium of a cell line.

In one embodiment, the affinity resin is capable of binding a glycoside-cleaving enzyme directly from conditioned medium of a cell line without manipulation of the conditioned medium.

In one embodiment, $R_1$ is CH$_2$OH, $R_2$, $R_3$, and $R_4$ are each OH, and $R_5$ is H or —OH.

In another embodiment, $R_1$ is CH$_2$OH, $R_2$ and $R_3$ are each OH, $R_4$ is —NH—C(O)—CH$_3$, and $R_5$ is H.

In yet another embodiment, $R_1$ is H, $R_2$ is CH$_2$OH, $R_3$ and $R_4$ are each OH, and $R_5$ is H.

In one embodiment, the functional group is —C(O)N—.

In one embodiment, the functional group is —O—.

In one embodiment, the linker is a straight chained, branched or cyclic aliphatic $C_2$-$C_{20}$ hydrocarbon optionally containing 1-8 heteroatoms selected from halogen, O, N, and S and combinations thereof.

In one embodiment, the linker is a straight chained aliphatic $C_2$-$C_{10}$ hydrocarbon.

In one embodiment, the linker is a straight chained aliphatic $C_5$ hydrocarbon.

In one embodiment, the affinity resin of the invention has the formula:

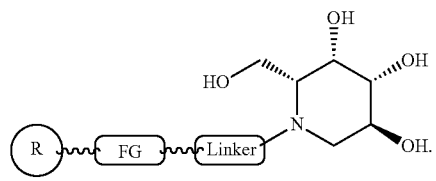

In one embodiment, the affinity resin has the formula:

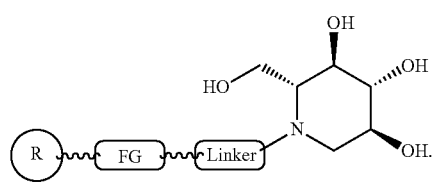

In one embodiment, the affinity resin has the formula:

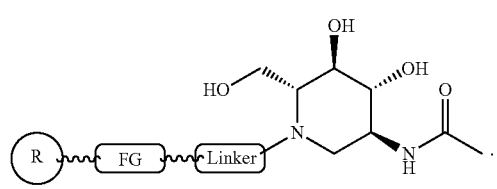

In one embodiment, the affinity resin has the formula:

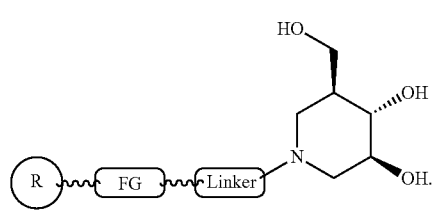

In one embodiment, the affinity resin has the formula:

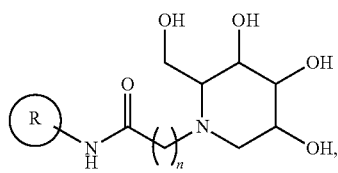

wherein R is a resin matrix and n is an integer from 2 to 20.

In one embodiment, n is 5.

In one aspect, an affinity resin is provided, comprising a small molecule ligand having the formula:

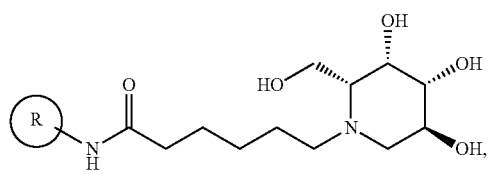

wherein R is a resin matrix.

In one aspect, an affinity resin is provided, comprising a small molecule ligand having the formula:

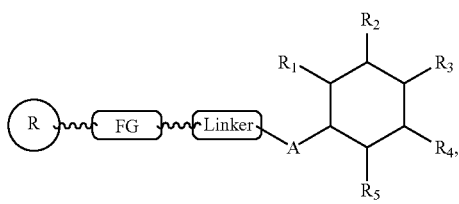

wherein R is a resin matrix;
FG is absent or is a functional group selected from —O—, —NH—, —C(O)N—, —C(O)O—, $CH_2$, and —S—;
Linker is absent or is selected from a straight chained, branched or cyclic aliphatic $C_2$-$C_{20}$ hydrocarbon; a heteroaliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S and combinations thereof;
A is selected from —NH— and —S—;
$R_1$, $R_2$, $R_3$, $R_4$, and $R_5$ are each independently selected from H, OH, $CH_2OH$, and —NH—C(O)—$CH_3$, and
wherein the affinity resin is capable of binding a glycoside-cleaving enzyme.

In some embodiments, the affinity resin is capable of binding a glycoside-cleaving enzyme from conditioned medium of a cell line.

In one embodiment, the affinity resin is capable of binding a glycoside-cleaving enzyme directly from conditioned medium of a cell line without manipulation of the conditioned medium.

In one embodiment, $R_1$, $R_2$, $R_3$, $R_4$, and $R_5$ are each OH.

In one embodiment, $R_1$ is $CH_2OH$, $R_2$ and $R_3$ are each OH, $R_4$ is —NH—C(O)—$CH_3$, and $R_5$ is H.

In one embodiment, the linker is a straight chained, branched or cyclic aliphatic $C_2$-$C_{20}$ hydrocarbon optionally containing 1-8 heteroatoms selected from halogen, O, N, and S and combinations thereof.

In one embodiment, the linker is a straight chained aliphatic $C_2$-$C_{10}$ hydrocarbon.

In one embodiment, A is —NH—.

In one embodiment, A is —S—.

In one embodiment, the affinity resin has the formula:

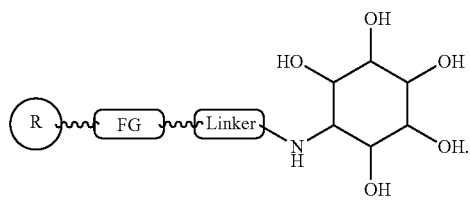

In one embodiment, the affinity resin has the formula:

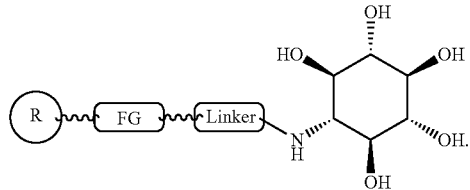

In another embodiment, the affinity resin has the formula:

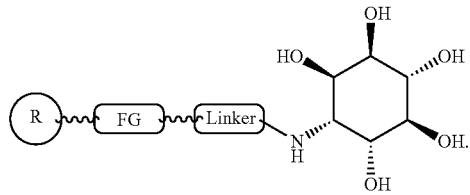

In another embodiment, the affinity resin has the formula:

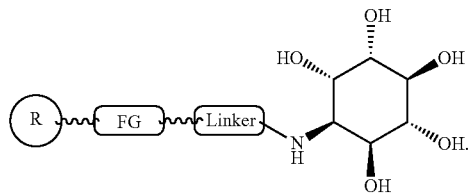

In yet another embodiment, the affinity resin has the formula:

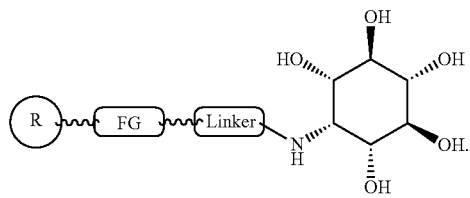

In yet another embodiment, the affinity resin has the formula:

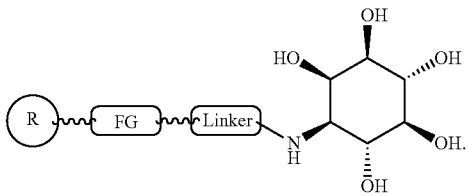

In one embodiment, the affinity resin according to any of the above embodiments has a binding capacity of at least 10 mg of glycoside-cleaving enzyme per 1 mL of the affinity resin.

In one embodiment, the affinity resin according to any of the above embodiments has a binding capacity of about 50 mL to about 100 mL of the conditioned medium per 1 mL of the affinity resin. In one embodiment, the affinity resin according to any of the above embodiments has a binding capacity of about 80 mL of the conditioned medium per 1 mL of the affinity resin.

In one embodiment, the affinity resin according to any of the above embodiments maintains purification performance after exposure to NaOH.

In one aspect of the present invention, a method of purifying a glycoside-cleaving enzyme produced in a cell line is provided, said method comprising the steps of binding the glycoside-cleaving enzyme to the affinity resin of any of the above embodiments, and eluting the bound glycoside-cleaving enzyme.

In one embodiment, the glycoside-cleaving enzyme is purified from conditioned medium.

In one embodiment, the glycoside-cleaving enzyme is purified directly from conditioned medium without manipulation of the conditioned medium.

In one aspect of the present invention, a method of purifying a glycoside-cleaving enzyme produced in a cell line, e.g., directly from conditioned medium of the cell line, e.g., without manipulation of the conditioned medium is provided, said method comprising the steps of binding the glycoside-cleaving enzyme to the affinity resin of any of the above embodiments, and eluting the bound glycoside-cleaving enzyme.

In one embodiment of the above method, the cell line is a recombinant CHO cell line.

In one embodiment of the above method, the cell line is a human cell line.

In one embodiment of the above method, the purity of the eluted glycoside-cleaving enzyme is at least 95%.

In one embodiment of the above method, the binding capacity of the affinity resin is at least 10 mg of glycoside-cleaving enzyme per 1 mL of the affinity resin.

In one embodiment of the above method, the glycoside-cleaving enzyme is selected from α-galactosidase A (α-Gal A), glucocerebrosidase (GCB), β-galactosidase, and acid alpha-glucosidase (GAA).

In one embodiment of the above method, the glycoside-cleaving enzyme is α-Gal A.

In one embodiment of the above method, the glycoside-cleaving enzyme is GCB.

In one embodiment of the above method, the glycoside-cleaving enzyme is GAA. In one embodiment, the step of eluting the bound glycoside-cleaving enzyme is performed with an elution buffer having a pH between about pH 5 and about pH 9. In one embodiment, the step of eluting the bound glycoside-cleaving enzyme is performed with an elution buffer having a pH between about pH 7 and about pH 8.5.

In one embodiment, the step of eluting the bound glycoside-cleaving enzyme is performed with an elution buffer comprising a salt. In one embodiment, the salt is NaCl. In one embodiment, the step of eluting the bound glycoside-cleaving enzyme is performed with an elution buffer comprising a different concentration of salt than the concentration found in the medium or buffer in which the enzyme bound to the affinity resin.

In one embodiment, the step of eluting the bound glycoside-cleaving enzyme is performed with an elution buffer comprising a small molecule ligand, which small molecule ligand is a competitive inhibitor of the bound glycoside-cleaving enzyme. In one embodiment, the small molecule ligand present in the elution buffer is the same small molecule ligand as immobilized on the affinity matrix. In another embodiment, the small molecule ligand present in the elution buffer is a different small molecule ligand from the small molecule ligand immobilized on the affinity matrix.

In one embodiment of the above method, the step of eluting the bound glycoside-cleaving enzyme is performed with an elution buffer comprising tris(hydroxymethyl) aminomethane (Tris).

In one aspect of the present invention, a method of purifying α-Gal A is provided, said method comprising the steps of binding the α-Gal A to the affinity resin of any of the above embodiments, and eluting the bound α-Gal A.

In one embodiment, a method of purifying α-Gal A directly from conditioned medium of a cell line is provided, said method comprising the steps of binding the α-Gal A to the affinity resin of any of the above embodiments, and eluting the bound α-Gal A.

In one embodiment, the α-Gal A is purified directly from conditioned medium of a cell line without manipulation of the conditioned medium.

In one embodiment, a method of purifying GCB directly from conditioned medium of a cell line is provided, said method comprising the steps of binding the GCB to the affinity resin of any of the above embodiments, and eluting the bound GCB.

In one embodiment, the GCB is purified directly from conditioned medium of a cell line without manipulation of the conditioned medium.

In one embodiment, a method of purifying GAA directly from conditioned medium of a cell line is provided, said method comprising the steps of binding the GAA to the affinity resin of any of the above embodiments, and eluting the bound GAA.

In one embodiment, the GAA is purified directly from conditioned medium of a cell line without manipulation of the conditioned medium.

In one embodiment, the step of eluting the bound glycoside-cleaving enzyme is performed with an elution buffer comprising tris(hydroxymethyl) aminomethane (Tris).

These and other aspects of the present invention will become apparent to those skilled in the art after a reading of the following detailed description of the invention, including the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows results of initial α-Gal A affinity purification testing.

FIG. 4 shows results of the affinity resin binding capacity testing.

FIG. 5 shows results of the affinity resin stability against sanitization testing.

DETAILED DESCRIPTION

Figure 1:
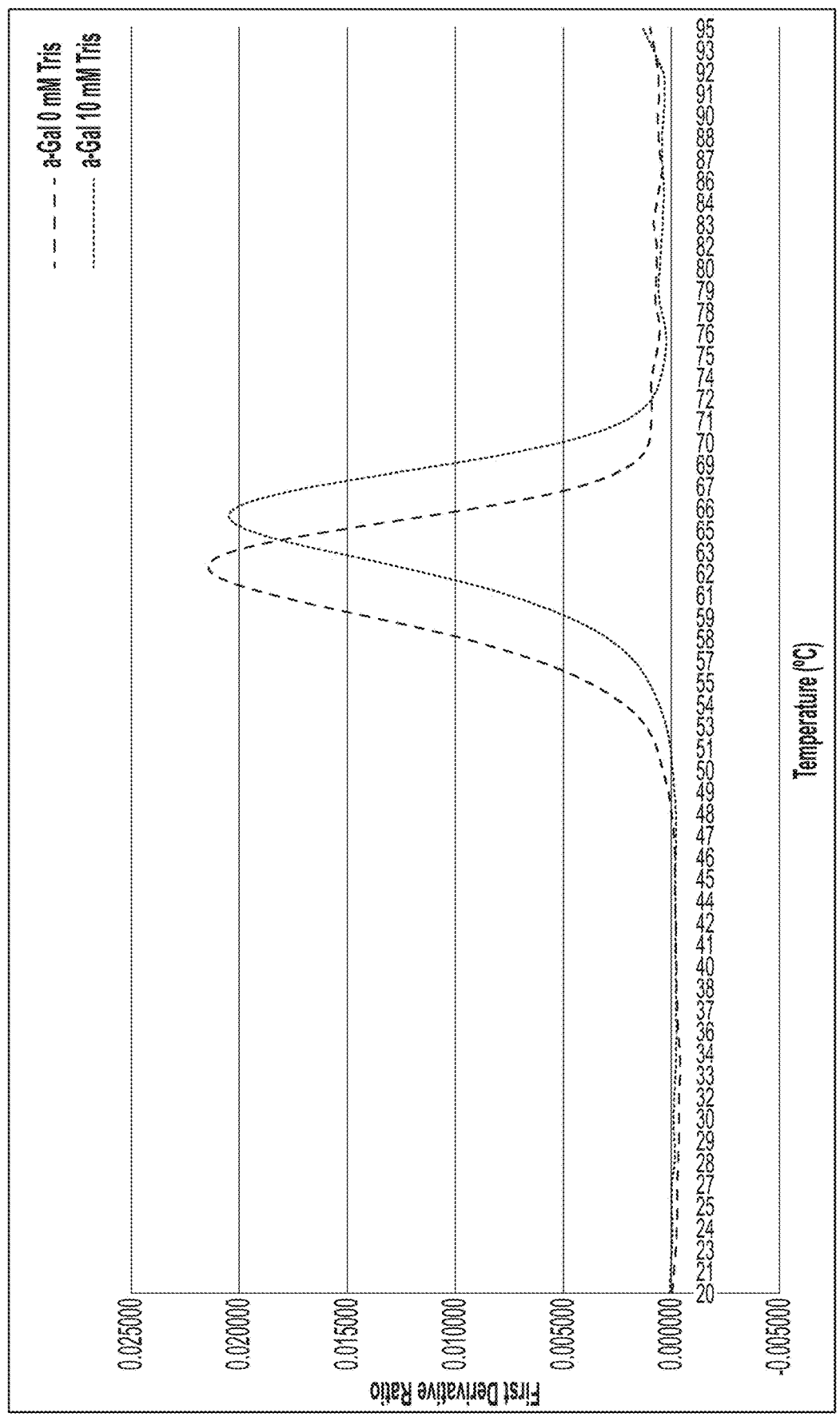
FIG. 1 depicts Thermal Stability curves of α-Gal A at 0 mM (blue) and 10 mM (red) Tris buffer.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Glycoside-Cleaving Enzyme Production

As described above, individuals with glycoside-cleaving enzyme deficiency, e.g., α-Gal A deficiency, GCB deficiency, or GAA deficiency, can be treated with purified glycoside-cleaving enzyme, e.g., α-Gal A, GCB, or GAA (i.e., enzyme replacement therapy). Cell lines, e.g., mammalian cell lines, e.g., CHO or human cell lines, or plant cell lines, genetically modified to overexpress the human glycoside-cleaving enzyme, e.g., α-Gal A, GCB, or GAA, may be used for in vitro protein production, to produce the glycoside-cleaving enzyme, e.g., α-Gal A, GCB, or GAA, which may be purified for enzyme replacement therapy. Secondary or immortalized human cells may be used and may be genetically modified by the transfection or transduction methods described elsewhere (see, e.g., PCT/US00/06118, U.S. Pat. No. 6,458,574, PCT/US97/16603, USSN 2011/0280856, U.S. Pat. No. 7,833,742). After genetic modification, the cells are cultured under conditions permitting overexpression and secretion of the human glycoside-cleaving enzyme, e.g., α-Gal A, GCB, or GAA.

The protein is isolated from the cultured cells, e.g., by collecting the medium in which the cells are grown, and/or lysing the cells to release their contents, concentrating the medium (e.g., by diafiltration/ultrafiltration), and then applying standard protein purification techniques, such as passing the protein through, e.g., a hydrophobic interaction resin, an ion exchange resin, e.g., an anion exchange or a cation exchange resin, or a mixed mode resin, and the like. Passing the sample over a resin may constitute the first chromatography step. Typically further purification is required, such as passing the glycoside-cleaving enzyme-containing material eluted from the hydrophobic interaction resin over a column containing a second resin, such as an immobilized heparin resin such as Heparin Sepharose®, hydroxyapatite, an anion exchange resin such as Q Sepharose®, or a size exclusion resin such as Superdex® 200.

As such, the present purification methodology has a number of serious drawbacks, such as requiring multi-step manipulation of raw material, requiring costly elution solutions, and/or not being easily scalable.

Affinity Resin Functionalized with Small Molecule Inhibitors

As disclosed in the present invention, it has been unexpectedly discovered that a variety of small molecules that bind to and/or inhibit glycoside-cleaving enzymes may be immobilized on solid support, i.e., conjugated to the solid matrix resin, and used effectively and efficiently for affinity column chromatography purification of glycoside-cleaving enzymes.

In one aspect, a small molecule capable of being immobilized may be an azasugar, i.e., a carbohydrate derivative in which a piperidine ring replaces a tetrahydrofuran ring, e.g., an iminosugar.

In one embodiment, the azasugar capable of being immobilized may have the following structural formula:

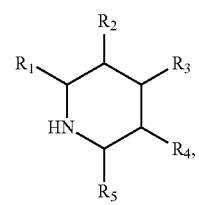

wherein $R_1$, $R_2$, $R_3$, $R_4$, and $R_5$ may be independently selected from H, OH, $CH_2OH$, and $-NH-C(O)-CH_3$.

In one particular embodiment, the azasugar capable of being immobilized may be an analog of DGJ, where DGJ has the following structural formula:

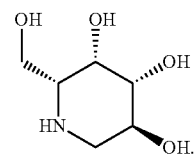 [SMILES: OC[C@H]1NC[C@H](O)[C@@H](O)[C@H]1O]

In another embodiment, the azasugar capable of being immobilized may have the following structural formula:

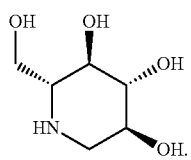 [SMILES: OC[C@H]1NC[C@H](O)[C@@H](O)[C@@H]1O]

In another embodiment, the azasugar capable of being immobilized may be an analog of isofagomine, where isofagomine has the following structural formula:

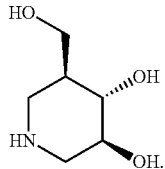

In one aspect of the present invention, an azasugar may be immobilized onto a solid support directly or via a linker or spacer, which linker or spacer may be covalently attached to the azasugar via the nitrogen atom of the carbohydrate ring, and further attached to a resin matrix directly or via a suitable functional group. In one embodiment, the azasugar immobilized onto a solid support may be represented by the following formula:

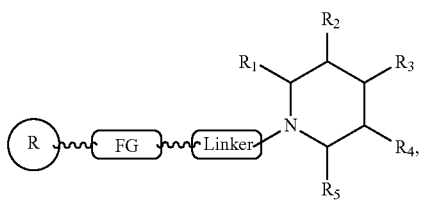

wherein R is a resin matrix;

FG is absent or is a functional group selected from —O—, —NH—, —C(O)N—, —C(O)O—, CH$_2$, and —S—; and Linker is absent or is selected from a straight chained, branched or cyclic aliphatic C$_2$-C$_{20}$ hydrocarbon; a heteroaliphatic C$_2$-C$_{20}$ hydrocarbon; an aromatic C$_6$-C$_{20}$ hydrocarbon; a heteroaromatic C$_2$-C$_{20}$ hydrocarbon; an aryl C$_6$-C$_{20}$ hydrocarbon; a heteroaryl C$_2$-C$_{20}$ hydrocarbon, a C$_2$-C$_{12}$ perfluorocarbon, or a combination thereof, each of which optionally contains 1-8 heteroatoms selected from halogen, O, N, and S and combinations thereof, and wherein R$_1$, R$_2$, R$_3$, R$_4$, and R$_5$ may be independently selected from H, OH, CH$_2$OH, and —NH—C(O)—CH$_3$.

In one embodiment, R$_1$ is CH$_2$OH, R$_2$, R$_3$, and R$_4$ are each OH, and R$_5$ is H.

In another embodiment, R$_1$ is CH$_2$OH, R$_2$ and R$_3$ are each OH, R$_4$ is —NH—C(O)—CH$_3$, and R$_5$ is H.

In another embodiment, R$_1$ is H, R$_2$ is CH$_2$OH, R$_3$ and R$_4$ are each OH, and R$_5$ is H.

In one embodiment, the functional group is —C(O)N—.
In one embodiment, the functional group is —O—.
In one embodiment, the linker is a straight chained, branched or cyclic aliphatic C$_2$-C$_{20}$ hydrocarbon optionally containing 1-8 heteroatoms selected from halogen, O, N, and S and combinations thereof.

In one embodiment, the linker is a straight chained aliphatic C$_2$-C$_{10}$ hydrocarbon.

In one embodiment, the linker is a straight chained aliphatic C$_5$ hydrocarbon.

In one embodiment, a DGJ analog may be N-5-Carboxypentyl-1-deoxygalactonojirimycin as shown in the following structure:

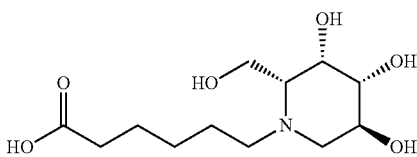 [SMILES: O=C(O)CCCCCN1C[C@H](O)[C@@H](O)[C@@H](O)[C@H]1CO]

N-5-Carboxypentyl-1-deoxygalactonojirimycin, conjugated to an affinity resin to generate a small molecule-based affinity purification chromatography resin.

In one embodiment, N-5-Carboxypentyl-1-deoxygalactonojirimycin may be immobilized onto a solid support and used for purification of glycoside-cleaving enzymes, e.g., α-Gal A, GCB, and GAA, by affinity chromatography. In one particular embodiment, N-5-Carboxypentyl-1-deoxygalactonojirimycin may be conjugated to an affinity resin and used for purification of α-Gal A by affinity chromatography, e.g., directly from the conditioned medium.

In another aspect, a small molecule capable of being immobilized may be a derivative of inositol, e.g., a derivative of Conduritol B epoxide, where Conduritol B epoxide has the following structural formula:

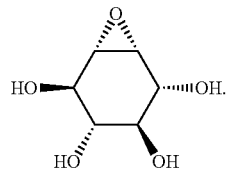 [SMILES: O[C@H]1[C@H](O)[C@@H](O)[C@@H]2O[C@@H]2[C@@H]1O]

In one embodiment, an inositol derivative, e.g., Conduritol B epoxide, may be immobilized on solid support by chemically reacting with an amino group on a resin matrix, giving a structure with an exo-cyclic amino group.

In another embodiment, an inositol derivative, e.g., Conduritol B epoxide, may be immobilized on solid support by chemically reacting with a sulfhydryl group on a resin matrix, giving a structure with an exo-cyclic thioether group.

In one aspect of the present invention, an inositol derivative may be immobilized onto a solid support directly or via a linker or spacer, which linker or spacer may be covalently attached to the inositol via, e.g., an amino group or a sulfhydryl group, and further attached to a resin matrix directly or via a suitable functional group. In one embodiment, the inositol derivative immobilized onto a solid support may be represented by the following formula:

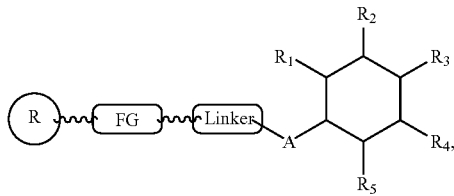

wherein R is a resin matrix;
FG is absent or is a functional group selected from —O—, —NH—, —C(O)N—, —C(O)O—, CH$_2$, and —S—;

Linker is absent or is selected from a straight chained, branched or cyclic aliphatic $C_2$-$C_{20}$ hydrocarbon; a heteroaliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S and combinations thereof;

A is selected from —NH— and —S—, and wherein $R_1$, $R_2$, $R_3$, $R_4$, and $R_5$ may be independently selected from H, OH, $CH_2OH$, and —NH—C(O)—$CH_3$.

In one embodiment, $R_1$, $R_2$, $R_3$, $R_4$, and $R_5$ are each OH.

In one embodiment, $R_1$ is $CH_2OH$, $R_2$ and $R_3$ are each OH, $R_4$ is —NH—C(O)—$CH_3$, and $R_5$ is H.

In one embodiment, the linker is a straight chained, branched or cyclic aliphatic $C_2$-$C_{20}$ hydrocarbon optionally containing 1-8 heteroatoms selected from halogen, O, N, and S and combinations thereof.

In one embodiment, the linker is a straight chained aliphatic $C_2$-$C_{10}$ hydrocarbon.

In one embodiment, the affinity resin has the formula:

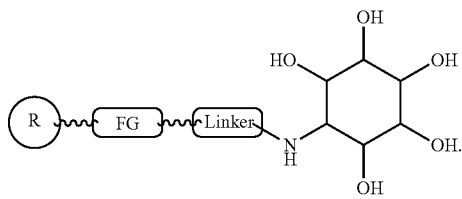

In one embodiment, the affinity resin has the formula:

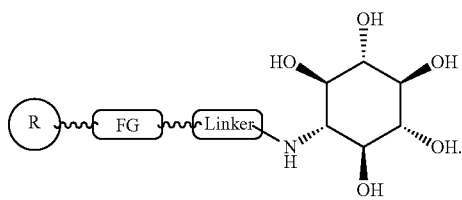

In another embodiment, the affinity resin has the formula:

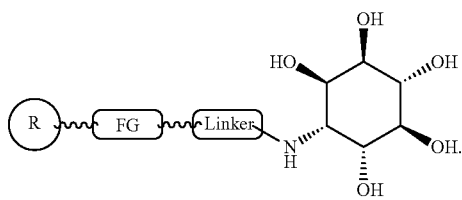

In another embodiment, the affinity resin has the formula:

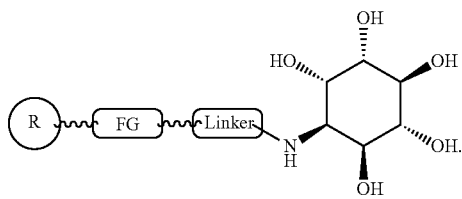

In yet another embodiment, the affinity resin has the formula:

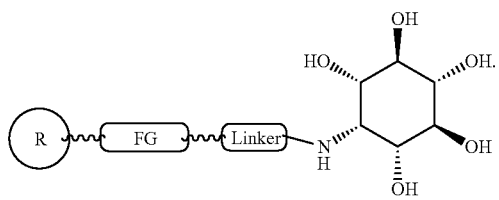

In yet another embodiment, the affinity resin has the formula:

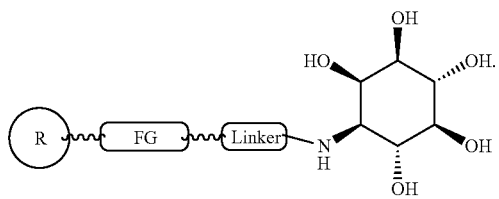

In one embodiment, the affinity resin according to any of the above embodiments has a binding capacity of at least 1 mg, or at least 2 mg, or at least 3 mg, or at least 4 mg, or at least 5 mg, or at least 6 mg, or at least 7 mg, or at least 8 mg, or at least 9 mg, or at least 10 mg, or at least 11 mg, or at least 12 mg, or at least 14 mg, or at least 16 mg of glycoside-cleaving enzyme per 1 mL of the affinity resin. In one embodiment, the affinity resin according to any of the above embodiments has a binding capacity of at least 10 mg of glycoside-cleaving enzyme per 1 mL of the affinity resin.

In one embodiment, the affinity resin according to any of the above embodiments has a binding capacity of at least 10 mL, or at least 20 mL, or at least 30 mL, or at least 40 mL, or at least 50 mL, or at least 60 mL, or at least 70 mL, or at least 80 mL, or at least 90 mL, or at least 100 mL of the conditioned medium per 1 mL of the affinity resin.

In one embodiment, the affinity resin according to any of the above embodiments has a binding capacity of about 10 mL to about 20 mL, or about 20 mL to about 40 mL, or about 40 mL to about 60 mL, or about 50 mL to about 100 mL, or about 60 mL to about 90 mL of the conditioned medium per 1 mL of the affinity resin.

In one embodiment, the affinity resin according to any of the above embodiments has a binding capacity of about 80 mL of the conditioned medium per 1 mL of the affinity resin.

In one embodiment, the affinity resin according to any of the above embodiments maintains purification performance after exposure to NaOH. In one embodiment, the affinity resin according to any of the above embodiments maintains purification performance after 30 min, or after 60 min, or after 90 min, or after 120 min, or after 150 min of exposure to NaOH.

In one embodiment, the affinity resin conjugated to a small molecule is capable of binding glycoside-cleaving enzymes, e.g., α-Gal A, GCB, and GAA, directly from conditioned medium of a cell line without any manipulation of the conditioned medium.

Elution Conditions

Various elution conditions including, without limitation, varying pH, addition of an ionic modifier, e.g., a salt, at a varying concentration, and addition of a small molecule competitive inhibitor at a varying concentration, may be employed for the step of eluting the bound glycoside-cleaving enzymes from the affinity column matrix according to the invention.

In some embodiments, varying pH conditions may be employed, including, without limitation, a buffer having a constant pH, a buffered pH gradient, and sequential elution buffers, each having a different pH. In one embodiment, the pH of the elution buffers may be between about pH 5 and about pH 9. In one embodiment, the pH of the elution buffer may be in the physiological pH range of about pH 7 to about pH 8.5.

In some embodiments, an ionic modifier, e.g., a salt, may be added to the elution solution, e.g., an elution buffer. In some embodiments, a suitable salt may have a cation selected from sodium, lithium, magnesium, calcium, and guanidinium, and an anion selected from chloride, nitrate, bromide, iodide, perchlorate, and chlorate. In one embodiment, the salt may be NaCl. The salt may be present at any concentration as determined optimal by one of skill in the art, for example from 0 mM to 1 M.

In some embodiments, small molecule competitive inhibitor ligands may be added to the elution solution, e.g., an elution buffer, to assist with elution of the bound glycoside-cleaving enzyme. By way of a non-limiting example, in some embodiments the small molecules that bind to and/or inhibit glycoside-cleaving enzymes, e.g., aza-sugar derivatives and/or inositol derivatives, may be added to the elution buffer.

In some embodiments, the small molecules that may be added to the elution buffer may be the same small molecule ligands as the ligands immobilized on the affinity matrix as described above. In some embodiments, the small molecules that may be added to the elution buffer may have the following structural formula:

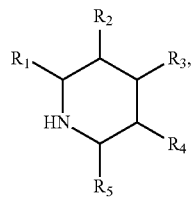

wherein $R_1$, $R_2$, $R_3$, $R_4$, and $R_5$ may be independently selected from H, OH, $CH_2OH$, and —NH—C(O)—$CH_3$.

In some embodiments, the small molecules that may be added to the elution buffer may be selected from:

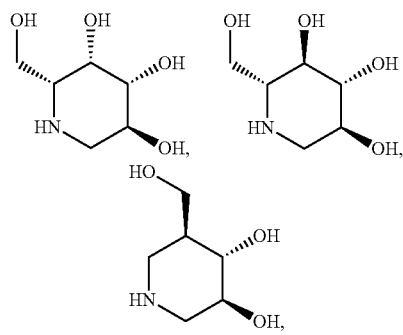

or pharmaceutically acceptable salts, esters, and derivatives thereof.

In some embodiments, the small molecules that may be added to the elution buffer may be a derivative of inositol, e.g., a derivative of Conduritol B epoxide, where Conduritol B epoxide has the following structural formula:

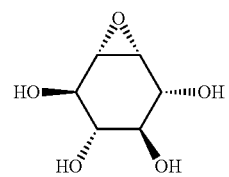

As stated above, in one embodiment, the step of eluting the bound glycoside-cleaving enzyme is performed with an elution buffer comprising a small molecule ligand, which small molecule ligand is a competitive inhibitor of the bound glycoside-cleaving enzyme. In one embodiment, the small molecule ligand present in the elution buffer is the same small molecule ligand as immobilized on the affinity matrix. In another embodiment, the small molecule ligand present in the elution buffer is a different small molecule ligand from the small molecule ligand immobilized on the affinity matrix.

Tris Elution Buffer

It has been noted by the authors of the present invention that the structure of tris(hydroxymethyl)aminomethane, also known as tromethamine or Tris, bears some similarities to the structure of the natural ligand of α-Gal A and the structure of the azasugar biomimetic DGJ, as shown below:

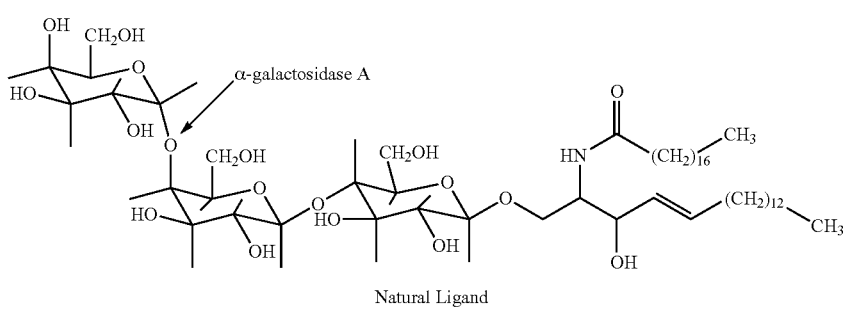

Natural Ligand

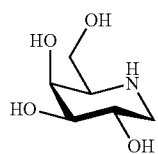
Biomimetic (Migalastat) Strong Binder (Single Digit nM KD)

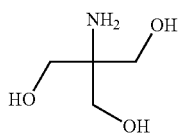
Biomimetic (Tris) Weak Binder (Triple Digit mM KD)

It has been discovered that α-Gal A thermal stability increases by 3° C. at 10 mM Tris (FIG. 1) and is dose concentration-dependent. Therefore, it has been hypothesized that Tris, a weak active site binder of α-Gal A, may be utilized as a competitive ligand to assist with the affinity chromatography purification of α-Gal A.

Figure 2:
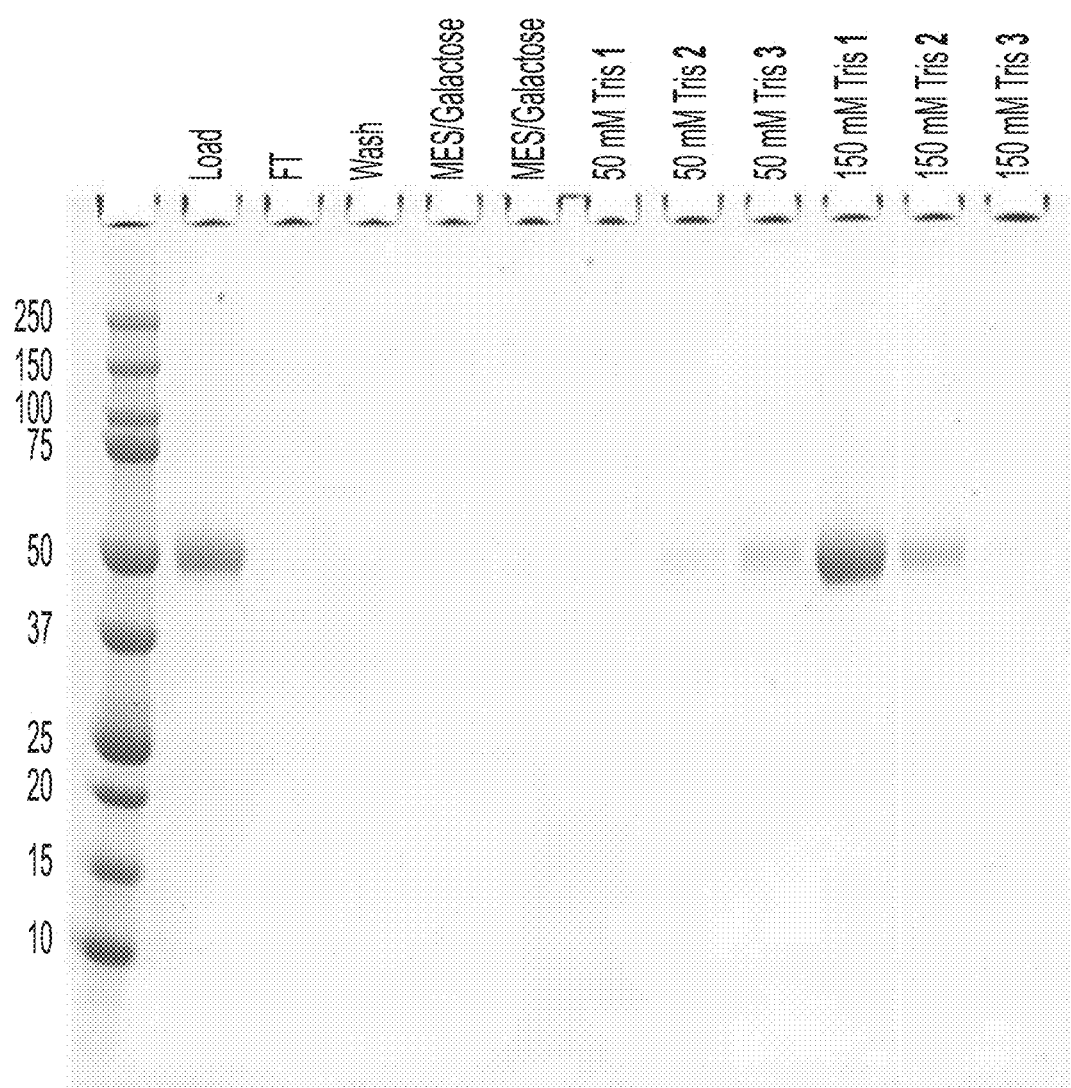
FIG. 2 shows an SDS-PAGE gel of α-Gal A affinity elution with Tris buffers.

It has been discovered that using a buffer comprising Tris at 150 mM α-Gal A is effectively eluted from the affinity resin (FIG. 2).

Purification Methods

In one aspect of the present invention, a method of purifying a glycoside-cleaving enzyme produced in a cell line is provided, said method comprising the steps of binding the glycoside-cleaving enzyme to the affinity resin as described above and eluting the bound glycoside-cleaving enzyme.

In one embodiment, a glycoside-cleaving enzyme is purified directly from conditioned medium of the cell line.

In one embodiment, a glycoside-cleaving enzyme is purified directly from conditioned medium of the cell line without manipulation of the conditioned medium.

For example, in some embodiments, a glycoside-cleaving enzyme is purified from conditioned medium which has not been subjected to one or more of: clarification, concentration (e.g., UF/DF), and pH alteration, following harvest.

As stated above, in some embodiments the method of the invention allows for the purification of a glycoside-cleaving enzyme, e.g., directly from conditioned medium of the cell line, e.g., without manipulation of the conditioned medium.

In one embodiment, the cell line may be a mammalian cell line. In one embodiment the cell line is a recombinant CHO cell line. In another embodiment, the cell line is a human cell line. In another embodiment, the cell line may be a plant cell line.

In one embodiment, the purity of the eluted glycoside-cleaving enzyme is at least 90%, or at least 95%, or at least 96%, or at least 97%, or at least 98%, or at least 99%, or at least 99.5%, or at least 99.8%, or 99.9%. In one embodiment, the purity of the eluted glycoside-cleaving enzyme is at least 95%.

In one embodiment, the binding capacity of the affinity resin is at least 1 mg, or at least 2 mg, or at least 3 mg, or at least 4 mg, or at least 5 mg, or at least 6 mg, or at least 7 mg, or at least 8 mg, or at least 9 mg, or at least 10 mg, or at least 11 mg, or at least 12 mg, or at least 14 mg, or at least 16 mg of glycoside-cleaving enzyme per 1 mL of the affinity resin. In one embodiment, the binding capacity of the affinity resin is at least 10 mg of glycoside-cleaving enzyme per 1 mL of the affinity resin.

In one embodiment, the affinity resin according to any of the above embodiments has a binding capacity of at least 10 mL, or at least 20 mL, or at least 30 mL, or at least 40 mL, or at least 50 mL, or at least 60 mL, or at least 70 mL, or at least 80 mL, or at least 90 mL, or at least 100 mL of the conditioned medium per 1 mL of the affinity resin.

In one embodiment, the affinity resin according to any of the above embodiments has a binding capacity of about 10 mL to about 20 mL, or about 20 mL to about 40 mL, or about 40 mL to about 60 mL, or about 50 mL to about 100 mL, or about 60 mL to about 90 mL of the conditioned medium per 1 mL of the affinity resin.

In one embodiment, the affinity resin according to any of the above embodiments has a binding capacity of about 80 mL of the conditioned medium per 1 mL of the affinity resin.

In one embodiment, the glycoside-cleaving enzyme capable of being purified by the method of the invention is selected from α-galactosidase A (α-Gal A), glucocerebrosidase (GCB), β-galactosidase, or GAA.

In one embodiment, the glycoside-cleaving enzyme is α-Gal A.

In another embodiment, the glycoside-cleaving enzyme is GCB.

In one embodiment, the step of eluting the bound glycoside-cleaving enzyme is performed with an elution buffer comprising tris(hydroxymethyl) aminomethane (Tris). In one embodiment, the step of eluting the bound glycoside-cleaving enzyme is performed with an elution buffer comprising 100 mM Tris, or 150 mM Tris, or 200 mM Tris, or 250 mM Tris, or 300 mM Tris, or 350 mM Tris, or 400 mM Tris, or 450 mM Tris, or 500 mM Tris.

In one aspect of the invention, a method of purifying α-Gal A is provided, said method comprising the steps of binding the α-Gal A to the affinity resin as described above and eluting the bound α-Gal A. In one embodiment, α-Gal A is purified directly from conditioned medium of a cell line. In one embodiment, α-Gal A is purified directly from conditioned medium of a cell line without manipulation of the conditioned medium.

In another aspect of the invention, a method of purifying GCB is provided, said method comprising the steps of binding GCB to the affinity resin as described above and eluting the bound GCB. In one embodiment, GCB is purified directly from conditioned medium of a cell line. In one embodiment, GCB is purified directly from conditioned medium of a cell line without manipulation of the conditioned medium.

In yet another aspect of the invention, a method of purifying GAA is provided, said method comprising the steps of binding GAA to the affinity resin as described above and eluting the bound GAA. In one embodiment, GAA is purified directly from conditioned medium of a cell line. In one embodiment, GAA is purified directly from conditioned medium of a cell line without manipulation of the conditioned medium.

Affinity Resin

In principle, any porous, beaded resin suitable for protein purification may be functionalized with small molecule inhibitors according to embodiments of the present invention using methods known in the art. Some examples of resins suitable for functionalization with small molecule inhibitors include, but are not limited to, CarboxyLink Resin (ThermoFisher), AminoLink Resin (ThermoFisher), Sulfo-Link Resin (ThermoFisher), Carbohydrate Coupling Resin (G-Biosciences), and the like.

One non-limiting example of a suitable resin is Carboxy-Link Resin, available from Thermo Scientific. CarboxyLink Coupling Resin may be used for covalent immobilization of peptides or other carboxyl-containing (—COOH) molecules to a porous, beaded resin for use in affinity purification procedures.

CarboxyLink Resin is crosslinked beaded agarose that has been activated with diamino-dipropylamine (DADPA) to contain long spacer arms, each with a primary amine at the end. When incubated with the resin and the carbodiimide crosslinker EDC (included in the CarboxyLink Immobilization Kit), carboxyl-containing molecules become permanently attached to the support by stable amide bonds. Once a molecule is coupled, the prepared affinity column can be used multiple times in typical protein affinity purification procedures. CarboxyLink Coupling Resins can also be used to immobilize other kinds of molecules using alternative amine-reactive crosslinking chemistries.

EXAMPLES

The following examples illustrate specific aspects of the instant description. The examples should not be construed as limiting, as the examples merely provide specific understanding and practice of the embodiments and their various aspects.

Example 1: DGJ-Resin Conjugation 30 mg of DGJ (Santa Cruz) was dissolved into 2.0 mL of 2-(N-morpholino) ethanesulfonic acid (MES)-based coupling buffer (0.1M MES, 0.9% NaCl, at pH=4). The mixture was added to 2 mL of Carboxylink Resin (ThermoFisher), which was pre-equilibrated with the coupling buffer, at 54 µmol/mL concentration of resin. The mixture was allowed to react for 3 hours with end-over-end rotation at room temperature, then placed at 4.0° C. overnight. The column was then drained of the post-coupling DGJ analog solution and washed with 5.0 C.V. of wash buffer. The column was then stored in PBS or equilibrated in relevant equilibration buffer for purification. Post-coupling DGJ Analog Solution was analyzed by 1D 1H NMR analysis to determine percent coupling of the DGJ Analog to the Carboxylink Resin, which was 84%. The small molecule-loaded resin was equilibrated with buffer prior to sample loading.

Figure 3A:
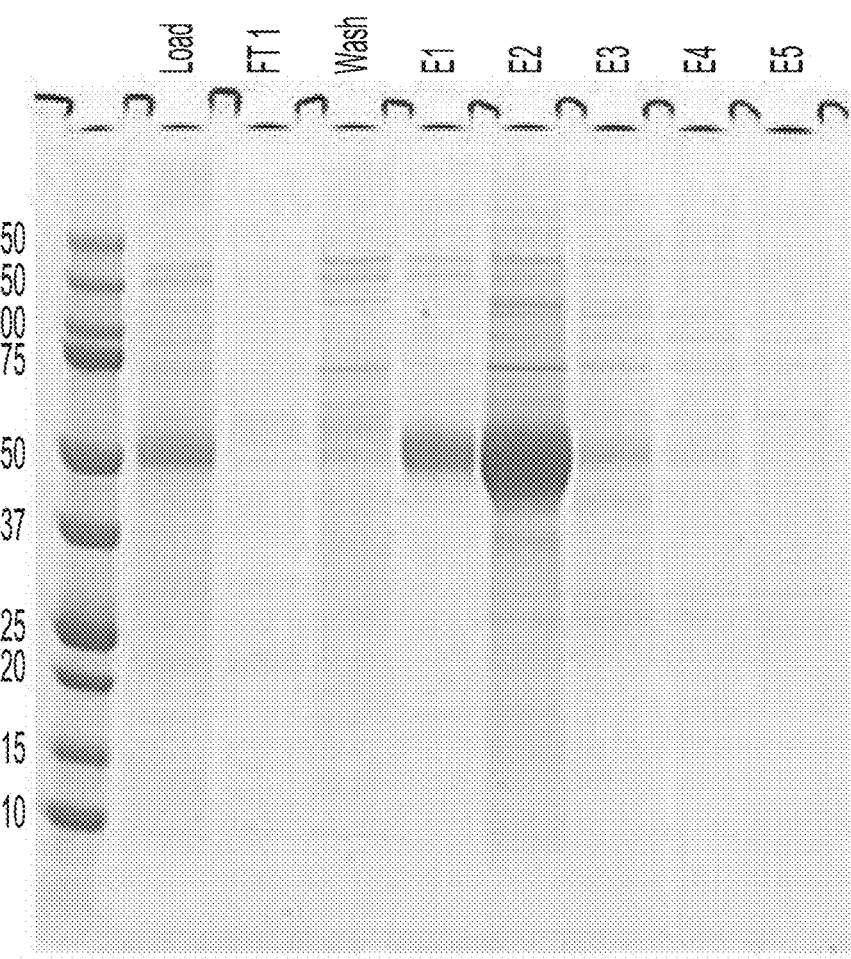
FIG. 3A shows an SDS-PAGE gel of initial α-Gal A affinity purification testing.
Figure 3B:
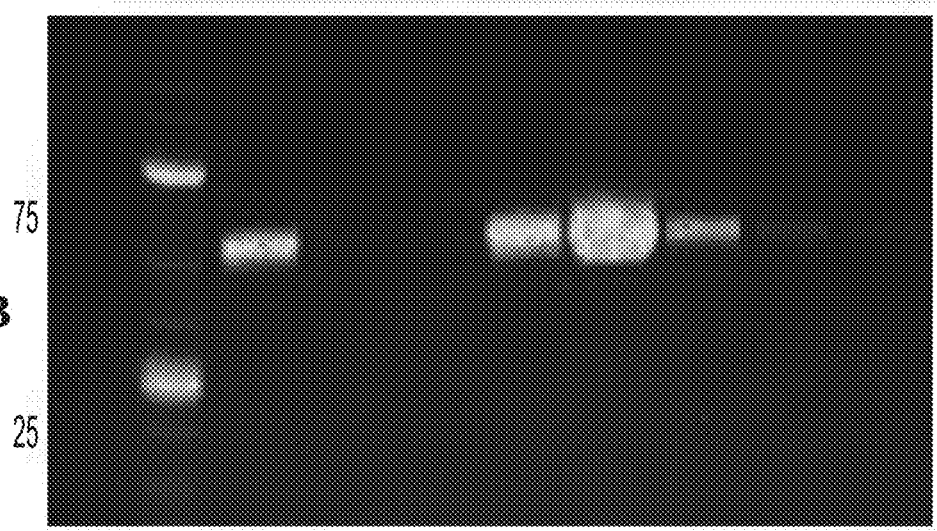
FIG. 3B shows anti-α-Gal A Western blot.

Example 2: Initial Testing of α-Gal a Purification Directly from Conditioned Medium Using DGJ-Conjugated Resin 2.0 mL DGJ-conjugated resin (54 µmol/mL DGJ) was equilibrated in 1×PBS (−/−) buffer. A sample of 40.0 mL of CHO α-Gal A conditioned medium (CM) was loaded onto the resin by gravity flow at concentration of 0.28 mg/mL. Total α-Gal A in crude CM was 11.2 mg. The column was washed with 10 C.V. of 1×PBS (−/−) buffer. α-Gal A was eluted with 5 C.V. of 150 mM tris(hydroxymethyl)aminomethane (Tris) elution buffer (pH=7.5), followed by 100 mM NaCl. Samples were evaluated by SDS-PAGE (FIG. 3A) and Western Blot (FIG. 3B). Total α-Gal A purified was 6.83 mg. Purity was 99% by HPLC, >90% by SDS-PAGE.

Initial testing demonstrated that utilizing a small molecule biomimetic based affinity column, and Tris based elution buffer, α-Gal A could be affinity purified directly from conditioned medium of a cell line without any manipulation of the conditioned medium. SDS-PAGE and Western Blot data demonstrated all of the α-Gal A in the 40.0 mL of the conditioned medium was captured by the DGJ analog affinity resin, resulting in 6-7 mg of affinity purified protein.

Figure 4A:
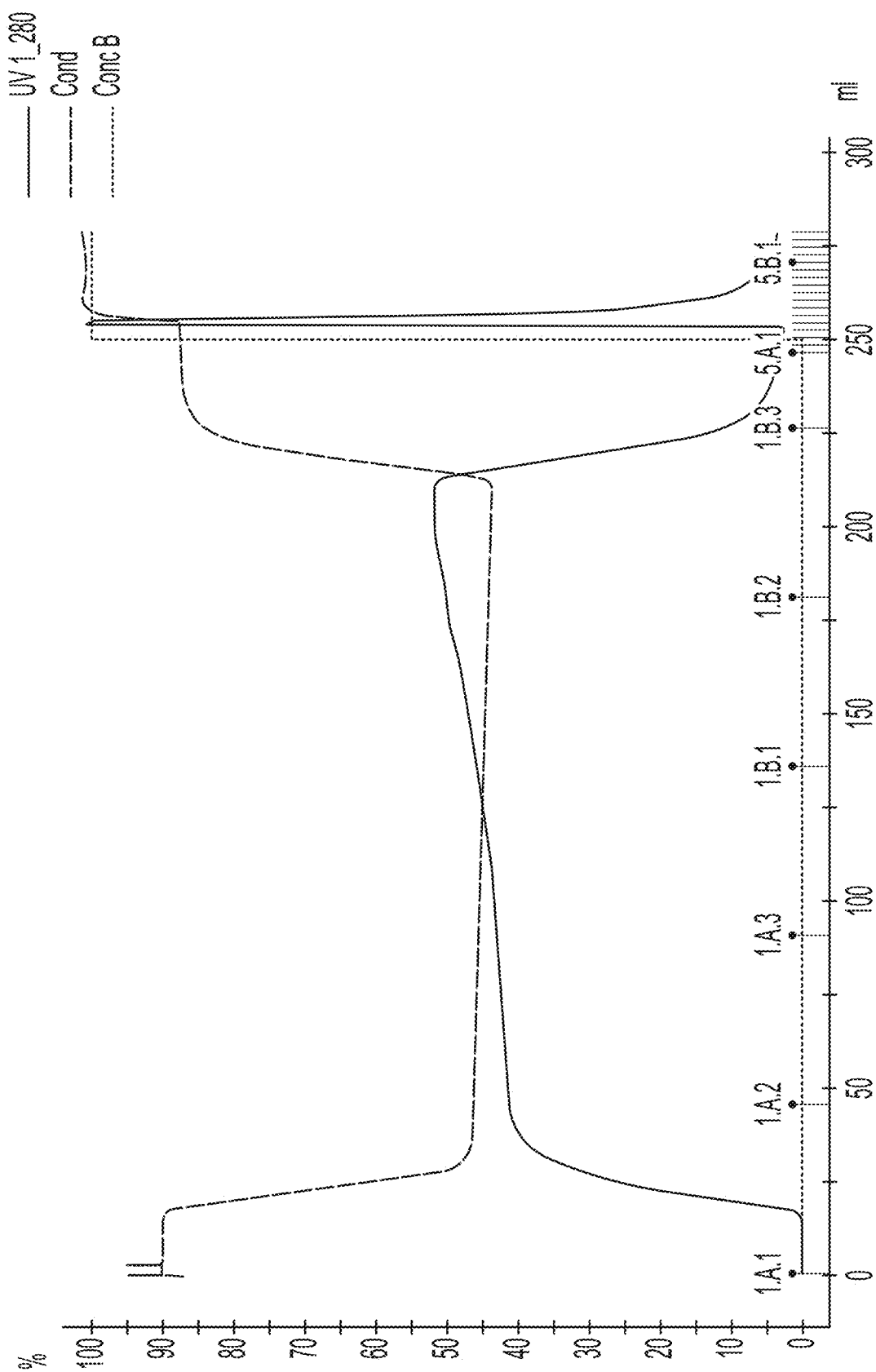
FIG. 4A shows a chromatogram of α-Gal A affinity resin binding capacity testing.
Figures 4B, 4C:
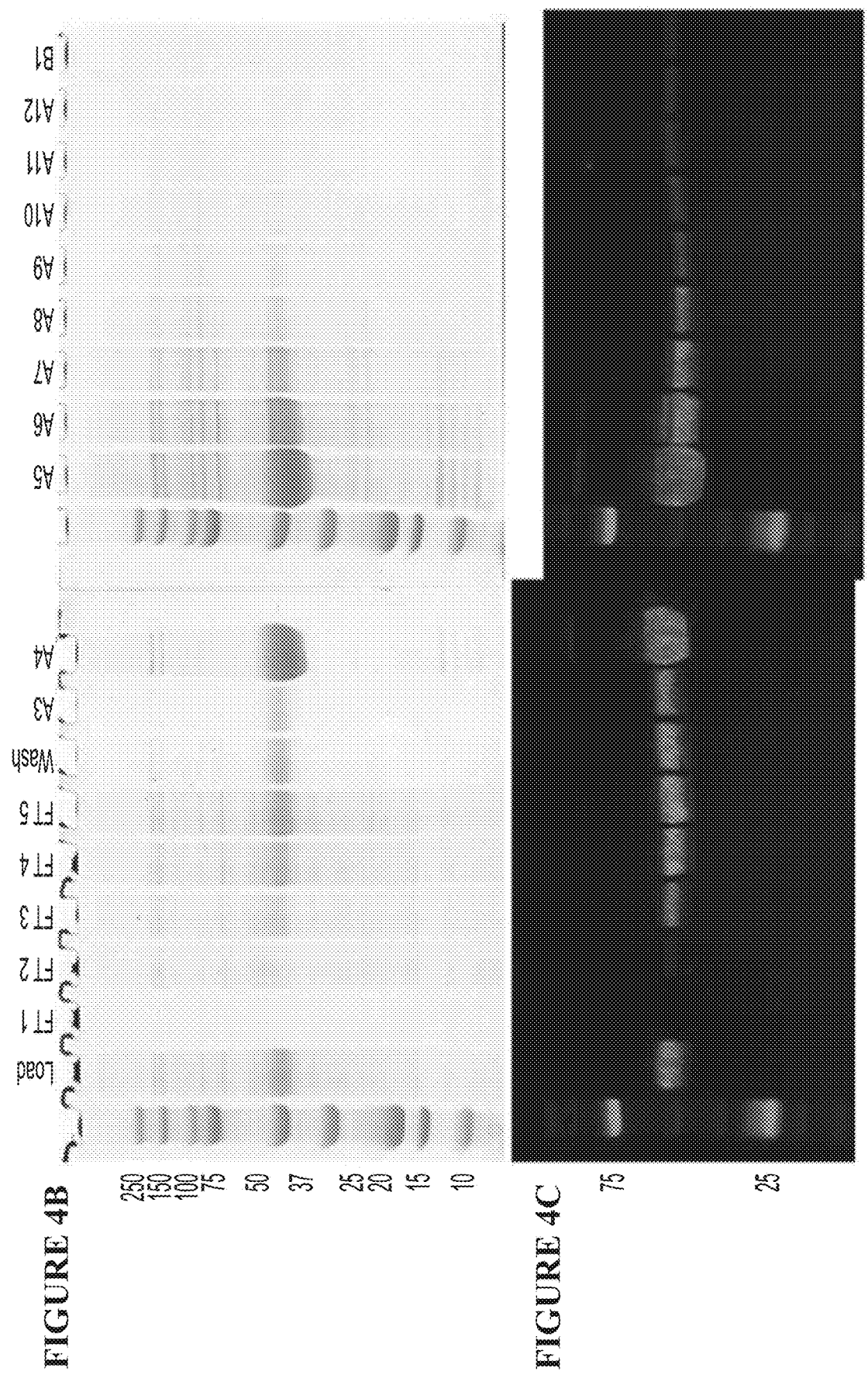
FIG. 4B shows an SDS-PAGE gel of α-Gal A affinity resin binding capacity testing.
FIG. 4C shows an anti-α-Gal A Western blot of α-Gal A affinity resin binding capacity testing.

Example 3: Capacity Testing of α-Gal a Purification Directly from Conditioned Medium Using DGJ-Conjugated Resin To determine the binding capacity of the affinity resin, the load was increased from 40 mL to 200 mL of neat conditioned medium with the goal to overload the column and to determine the approximate binding capacity of the column. Based on UV (280 nm) absorbance (FIG. 4A), SDS-PAGE (FIG. 4B), and Western Blot (FIG. 4C) analysis, α-Gal A broke through around 100 mL of conditioned medium, resulting in an approximate binding capacity of 16-17 mg of α-Gal A per mL of resin. As the resin was overloaded by design, it was expected to have some α-Gal A wash off, and α-Gal A was indeed found in the wash of the affinity column.

Example 4: Stability Against Sanitization

Figure 5A:
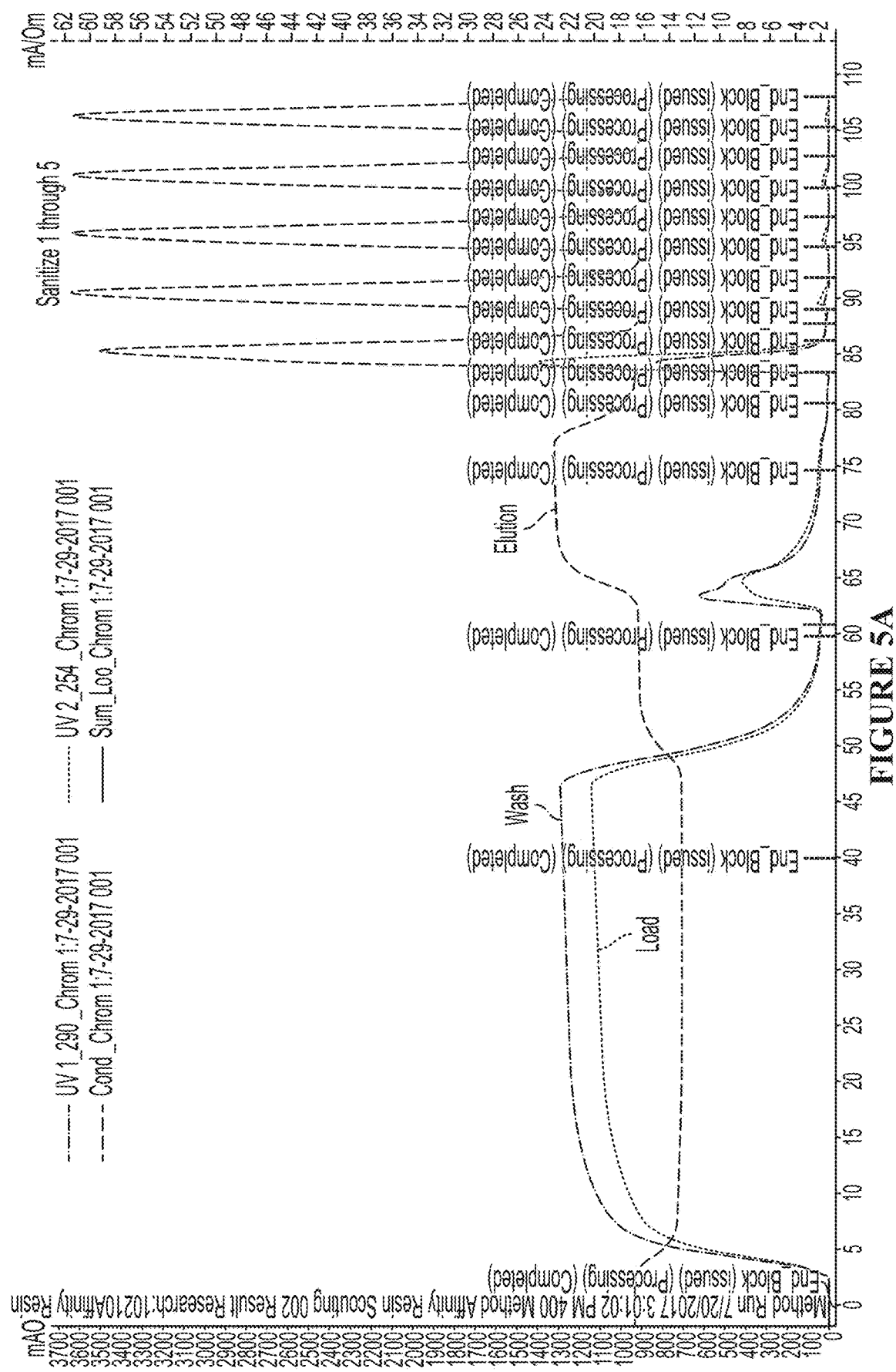
FIG. 5A is a chromatogram of the affinity resin stability against sanitization testing with five sanitization cycles.
Figure 5B:
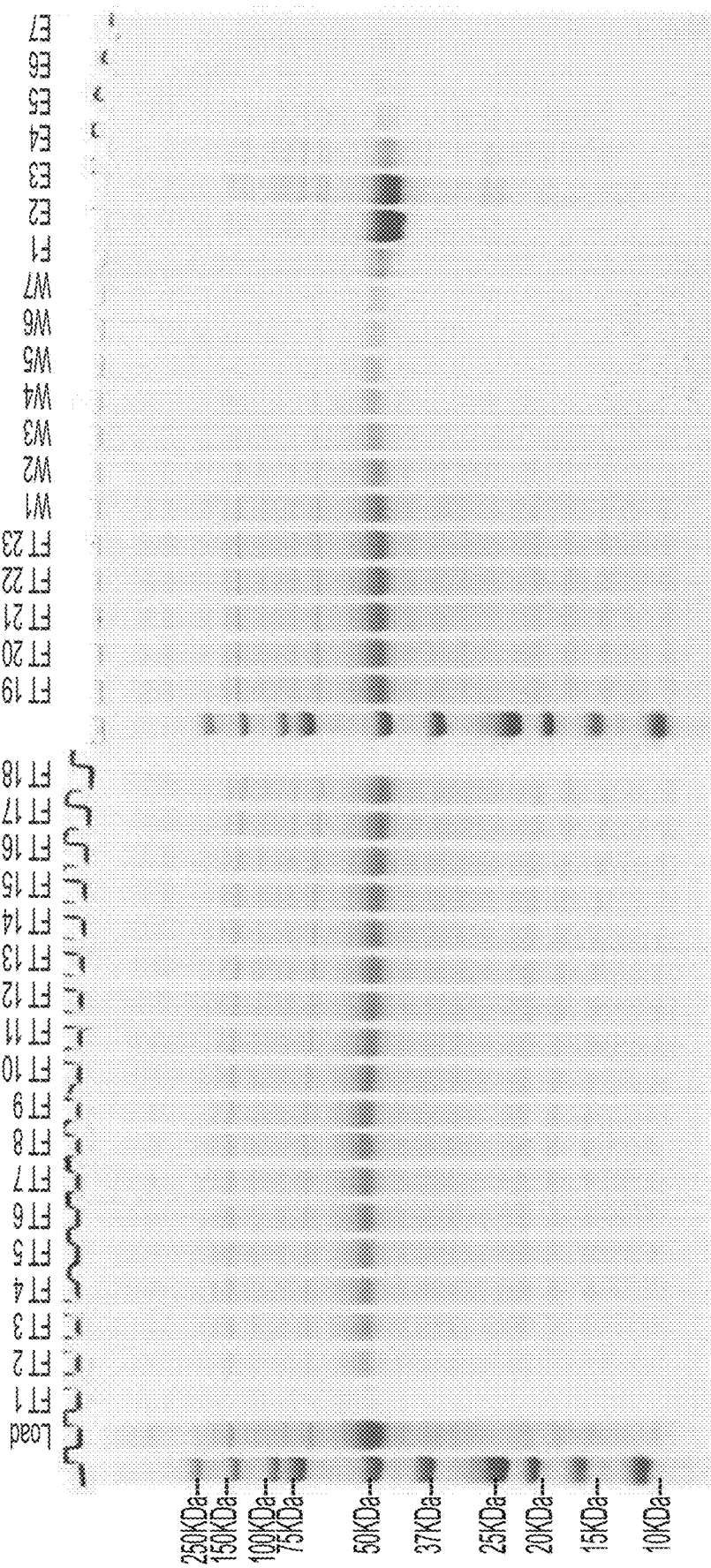
FIG. 5B is an SDS-PAGE gel of eluted α-Gal A.

To determine whether the DGJ analog would be able to maintain integrity over a significant amount of sodium hydroxide-based sanitization, which is a common sanitization method for conventional chromatography resin such as ion-exchange and hydrophobic resin, a study of resin performance after repeated NaOH sanitization was carried out. The method exposes the resin to 5×30-minute washes of 0.3 N NaOH, with neutralization between sanitization. This results in 2.5 hours of sanitization time per purification cycle. A total of 4 purification cycles were conducted to evaluate column performance over time. The chromatogram trace (FIG. 5A) and SDS-PAGE gel (FIG. 5B) analysis were very similar for each purification cycle. No loss of protein recovery was observed. Table 1, below, summarizes the total eluted protein quantitation over 4 purification cycles:

TABLE 1

| Total eluted Protein Quantification | |
|---|---|
| | Total Protein (mg) |
| Purification Cycle #1 | 4 |
| Purification Cycle #2 | 5.2 |
| Purification Cycle #3 | 3 |
| Purification Cycle #4 | 5.5 |
| Average over four cycles | 4.4 |

As Table 1, above, demonstrates, the average protein recovery was 4.4 mg/purification cycle. Overall, the data support the conclusion that the DGJ analog retains structural integrity over the course of the sanitization testing.

All of the α-Gal A protein purified from the DGJ-analog resin had the expected enzyme activity and biochemical and biophysical properties.

It has been demonstrated that DGJ analog affinity resin of the invention can bind α-Gal A protein directly from the conditioned medium without any manipulation of the conditioned medium. The binding capacity of the affinity resin has been shown to be about 80 mL of the conditioned medium per 1 mL of the resin. The protein binding capacity of the affinity resin has been shown to be about 16-17 mg of protein per 1 mL of the resin. The DGJ analog affinity resin of the invention maintains purification performance after a total of about 10 hours of exposure to NaOH.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A method of purifying a glycoside-cleaving enzyme produced in a cell line, said method comprising the steps of binding the glycoside-cleaving enzyme to an affinity resin comprising a small molecule ligand having the formula:

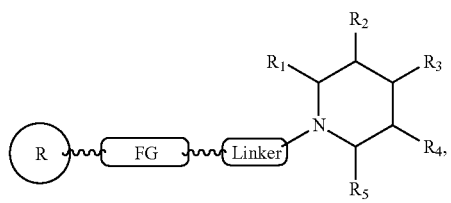

wherein R is a resin matrix;
FG is a functional group selected from —O—, —NH—, —C(O)N—, —C(O)O—, $CH_2$, and —S—;
Linker is selected from a straight chained, branched or cyclic aliphatic $C_2$-$C_{20}$ hydrocarbon; a heteroaliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S and combinations thereof;
$R_1$, $R_2$, $R_3$, $R_4$, and $R_5$ are each independently selected from H, OH, $CH_2OH$, and —NH—C(O)—$CH_3$, and wherein the affinity resin is capable of binding a glycoside-cleaving enzyme,
and eluting the bound glycoside-cleaving enzyme.

2. The method of claim 1, wherein the glycoside-cleaving enzyme is purified from conditioned medium.

3. The method of claim 1, wherein the glycoside-cleaving enzyme is purified directly from conditioned medium without manipulation of the conditioned medium.

4. The method of claim 1, wherein the cell line is a recombinant CHO cell line.

5. The method of claim 1, wherein the cell line is a human cell line.

6. The method of claim 1, wherein the purity of the eluted glycoside-cleaving enzyme is at least 95%.

7. The method of claim 1, wherein the binding capacity of the affinity resin is at least 10 mg of glycoside-cleaving enzyme per 1 mL of the affinity resin.

8. The method of claim 1, wherein the glycoside-cleaving enzyme is selected from α-galactosidase A (α-Gal A), glucocerebrosidase (GCB), β-galactosidase, and acid alpha-glucosidase (GAA).

9. The method of claim 1, wherein the step of eluting the bound glycoside-cleaving enzyme is performed with an elution buffer comprising tris(hydroxymethyl) aminomethane (Tris).

10. The method of claim 1, wherein the step of eluting the bound glycoside-cleaving enzyme is performed with an elution buffer comprising the same small molecule ligand as the small molecule ligand immobilized on the affinity matrix.

11. The method of claim 1, wherein the step of eluting the bound glycoside-cleaving enzyme is performed with an elution buffer having a pH between about pH 5 and about pH 9.

12. The method of claim 1, wherein the step of eluting the bound glycoside-cleaving enzyme is performed with an elution buffer comprising a salt.

13. The method of claim 12, wherein the salt is NaCl.

14. A method of purifying a glycoside-cleaving enzyme produced in a cell line, said method comprising the steps of binding the glycoside-cleaving enzyme to an affinity resin comprising a small molecule ligand having the formula:

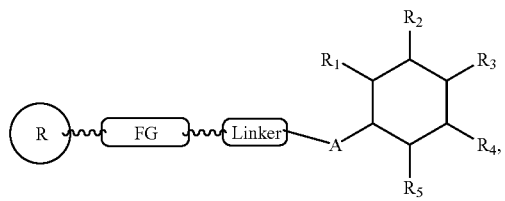

wherein R is a resin matrix;
FG is a functional group selected from —O—, —NH—, —C(O)N—, —C(O)O—, $CH_2$, and —S—;
Linker is selected from a straight chained, branched or cyclic aliphatic $C_2$-$C_{20}$ hydrocarbon; a heteroaliphatic $C_2$-$C_{20}$ hydrocarbon; an aromatic $C_6$-$C_{20}$ hydrocarbon; a heteroaromatic $C_2$-$C_{20}$ hydrocarbon; an aryl $C_6$-$C_{20}$ hydrocarbon; a heteroaryl $C_2$-$C_{20}$ hydrocarbon, a $C_2$-$C_{12}$ perfluorocarbon, or a combination thereof, each of which optionally contains 1-8 heteroatoms selected from halogen, O, N, and S and combinations thereof;
A is selected from —NH— and —S—;
$R_1$, $R_2$, $R_3$, $R_4$, and $R_5$ are each independently selected from H, OH, and —NH—C(O)—$CH_3$, and wherein the affinity resin is capable of binding a glycoside-cleaving enzyme,
and eluting the bound glycoside-cleaving enzyme.

15. The method of claim 1, wherein $R_1$ is $CH_2OH$, $R_2$, $R_3$, and $R_4$ are each OH, and $R_5$ is H.

16. The method of claim 1, wherein $R_1$ is $CH_2OH$, $R_2$ and $R_3$ are each OH, $R_4$ is —NH—C(O)—$CH_3$, and $R_5$ is H.

17. The method of claim 1, wherein $R_1$ is H, $R_2$ is $CH_2OH$, $R_3$ and $R_4$ are each OH, and $R_5$ is H.

18. The method of claim 1, wherein the functional group is —C(O)N—.

19. The method of claim 1, wherein the functional group is —O—.

20. The method of claim 1, wherein the linker is a straight chained, branched or cyclic aliphatic $C_2$-$C_{20}$ hydrocarbon optionally containing 1-8 heteroatoms selected from halogen, O, N, and S and combinations thereof.

21. The method of claim 1, wherein the linker is a straight chained aliphatic $C_2$-$C_{10}$ hydrocarbon.

22. The method of claim 1, wherein the linker is a straight chained aliphatic $C_5$ hydrocarbon.

23. The method of claim 1, wherein the affinity resin has the formula selected from the group consisting of:

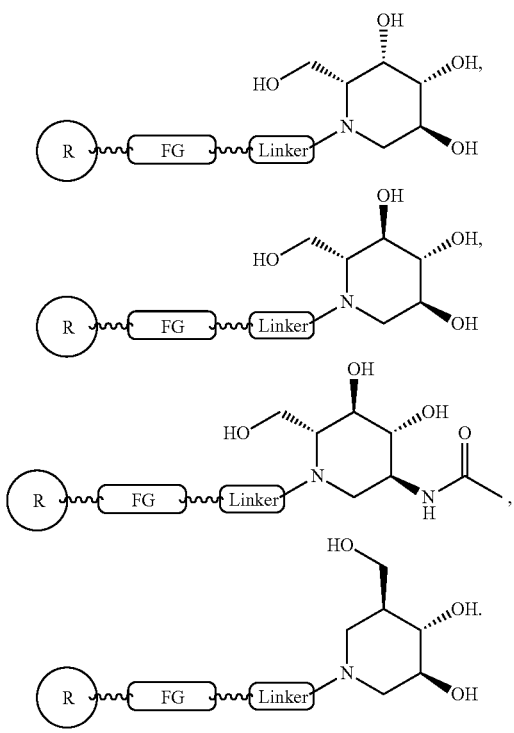

24. The method of claim 1, wherein the affinity resin has the formula:

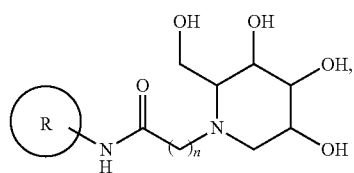

wherein R is a resin matrix and n is an integer from 2 to 20.

25. The method of claim 24, wherein n is 5.

26. The method of claim 1, wherein the affinity resin has the formula:

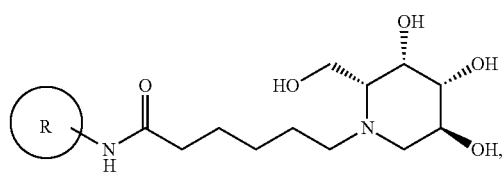

wherein R is a resin matrix.

27. The method of claim 14, wherein $R_1$, $R_2$, $R_3$, $R_4$, and $R_5$ are each OH.

28. The method of claim 14, wherein $R_1$ is $CH_2OH$, $R_2$ and $R_3$ are each OH, $R_4$ is —NH—C(O)—$CH_3$, and $R_5$ is H.

29. The method of claim 14, wherein A is —NH—.

30. The method of claim 14, wherein A is —S—.

31. The method of claim 14, wherein the linker is a straight chained, branched or cyclic aliphatic $C_2$-$C_{20}$ hydrocarbon optionally containing 1-8 heteroatoms selected from halogen, O, N, and S and combinations thereof.

32. The method of claim 14, wherein the linker is a straight chained aliphatic $C_2$-$C_{10}$ hydrocarbon.

33. The method of claim 14, wherein the affinity resin has the formula:

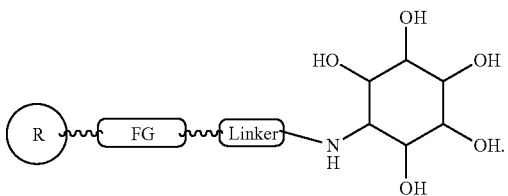

34. The method of claim 14, wherein the affinity resin has the formula selected from:

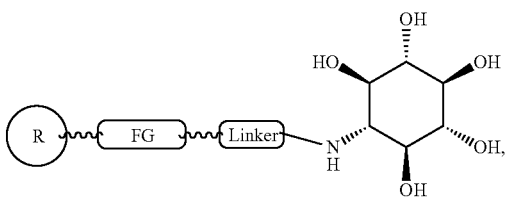

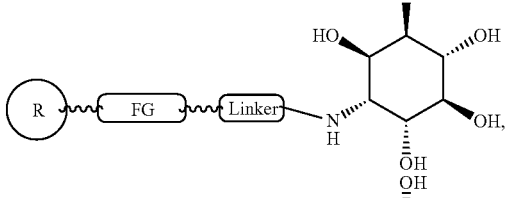

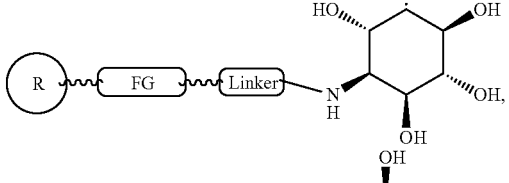

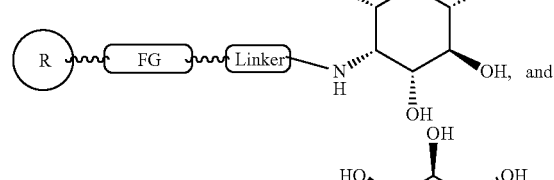

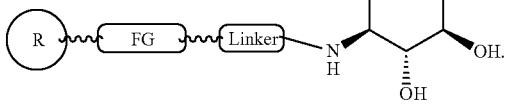

* * * * *